(12) United States Patent
Li et al.

(10) Patent No.: US 7,700,767 B2
(45) Date of Patent: Apr. 20, 2010

(54) SYSTEM AND PROCESS FOR PURIFYING AN AQUEOUS SOLUTION OF CRUDE CAPROLACTAM

(75) Inventors: Chien-Hsien Li, Taipei (TW); Shou-Li Luo, Taipei (TW)

(73) Assignee: China Petrochemical Development Corporation, Taipei (TW)

( * ) Notice: Subject to any disclaimer, the term of this patent is extended or adjusted under 35 U.S.C. 154(b) by 234 days.

(21) Appl. No.: 11/897,883

(22) Filed: Aug. 31, 2007

(65) Prior Publication Data

US 2008/0058513 A1    Mar. 6, 2008

(51) Int. Cl.
*C07D 223/04*    (2006.01)

(52) U.S. Cl. .................................................. 540/540

(58) Field of Classification Search .................. 540/540
See application file for complete search history.

*Primary Examiner*—Bruck Kifle
(74) *Attorney, Agent, or Firm*—Edwards Angell Palmer & Dodge LLP; Peter F. Corless; Dwight D. Kim

(57) ABSTRACT

A system for purifying an aqueous solution of crude caprolactam is provided, which includes a filtration zone (A), an inspection unit (B), a purification zone (C), and a first temporary storage tank (D). The filtration zone (A) contains a filtration apparatus though which an aqueous solution of crude caprolactam is filtered to remove ionic impurities therein, so as to obtain caprolactam-containing filtrate; the inspection unit (B) is used for judging the filtrate from the filtration zone (A) meets the preset inspection standards; the purification zone (C) is used for concentrating and further purifying filtrate meeting the preset inspection standards, thereby forming a final caprolactam product; and the first temporary storage tank (D) is used for receiving the filtrate not meeting the preset inspection standards, which is then mixed with the aqueous solution of crude caprolactam and delivered back to the filtration zone (A).

21 Claims, 5 Drawing Sheets

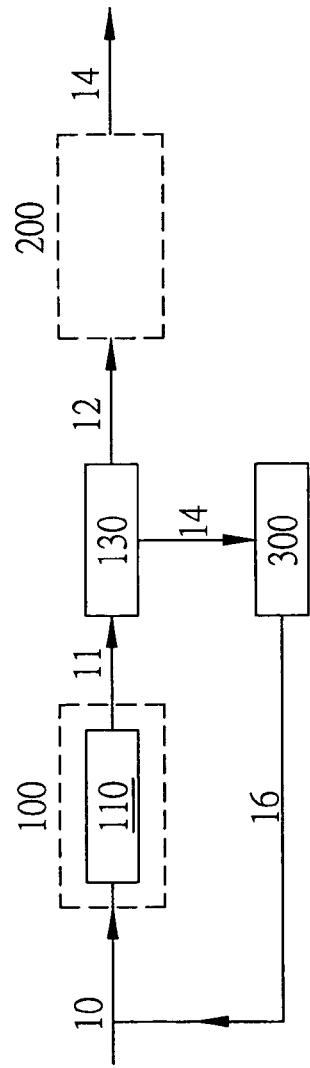
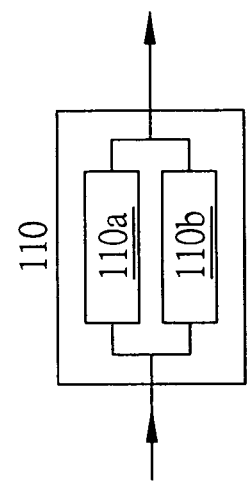
FIG. 1A
FIG. 1B

US 7,700,767 B2

SYSTEM AND PROCESS FOR PURIFYING AN AQUEOUS SOLUTION OF CRUDE CAPROLACTAM

BACKGROUND OF THE INVENTION

1. Field of the Invention

This invention relates to a system for purifying an aqueous solution of crude caprolactam, especially by a system using an ion-exchange resin apparatus.

2. Description of Related Art

Caprolactam is industrially produced by, for example, a process including subjecting cyclohexanone oxime to an oleum-catalyzed Beckmann rearrangement reaction to form caprolactam; neutralizing the resulting reaction mixture containing oleum and caprolactam with ammonia water; and separating caprolactam from the formed ammonium sulfate. Usually, the separation is achieved, first, by extracting the mixture with an organic solvent, and then extracting the caprolactam-containing organic phase with water to obtain an aqueous solution of crude caprolactam, which contains about 30% to 40% of caprolactam.

Because caprolactam is an important starting material for synthesis of polyamide, the aqueous solution of crude caprolactam should be further purified to meet the high purity standards for caprolactam of industrial grade. So far, a variety of purification methods for obtaining caprolactam with high purity have been proposed, for example, purification by recrystallization, ion exchange by using an ion-exchange resin, distillation, etc. Among these methods, the method using ion-exchange resin is preferable, because it is very effective in removing ionic impurities from the aqueous solution of crude caprolactam.

FIG. 5 shows a flow chart of purifying crude caprolactam according to the prior art. First, an aqueous solution of crude caprolactam containing 30 to 40% of caprolactam, water, and impurities was delivered via a pipeline 10 to an ion-exchange apparatus set 110 composed of a tower comprising a cation-exchange resin and a tower comprising an anion-exchange resin, where the aqueous solution of crude caprolactam was filtered through the ion-exchange apparatus set 110 to remove the ionic impurities therein. Next, the filtered aqueous solution of crude caprolactam (also referred to as "filtrate" hereinafter) was delivered via a pipeline 12 to a vaporization apparatus 210, where the filtrate was concentrated to obtain a concentrated filtrate containing a high concentration (for example, higher than 80%) of caprolactam. The concentrated filtrate was delivered via a pipeline 14 to a buffer apparatus 220, and then delivered via a pipeline 16 to a distillation apparatus 230, where the concentrated filtrate was further purified, thereby obtaining a final caprolactam product with a high-purity. The final caprolactam product was then recovered through a pipeline 18.

It was necessary to provide an inspection unit at the outlet of the ion-exchange apparatus set to judge whether the filtrate from the ion-exchange apparatus set met the preset inspection standards, thereby assuring that the final caprolactam product always met the standards for caprolactam of industrial grade. The preset inspection standards include the absorbance of the industrial caprolactam at a wavelength of 290 nm (EXT.290) and/or alkaline (ALK), as a standard for inspecting caprolactam-containing filtrate. If the EXT.290 and/or the ALK. of the filtrate exceed the preset upper limits for EXT. 290 and ALK, the quality of the final caprolactam product obtained from the subsequent distillation steps would deteriorate and could not meet the standard of "EXT.290 below 0.05" for caprolactam of industrial grade. Therefore, it was necessary to temporarily stop the filtration operation and replace the ion exchange apparatus before the EXT.290 and/or ALK of the filtrate exceed the upper limits.

However, the inventor of this invention first found that the EXT.290 and/or the ALK of the filtrate, after the aforesaid abrupt rising, would decrease back to the value before the abrupt rising (ie., the values below the preset upper limits) when the ion-exchange apparatus continued running. Thereafter, the EXT.290 and/or the ALK of the filtrate would steadily and slowly increase and remained below the upper limits for a relatively long period of time. In other words, after the EXT.290 and/or the ALK of the filtrate at the outlet of the ion-exchange apparatus abruptly rose and then decreased back, the ion-exchange apparatus could effectively operate for a relatively long period of time and the obtained final caprolactam product that still meets the standards for caprolactam of grade. The currently used ion-exchange resin purification process usually performs the resin replacement process before the EXT.290 and/or the ALK abruptly rise, to avoid producing a final caprolactam product that does not meet the standards. Frequent resin replacement and regeneration process use a large amount of acid, base, and water, and produce a large amount of sewage to be treated.

In view of the above, the inventor of this invention proposes a new system which allows the ion-exchange apparatus to continue running even if the abrupt rising in the EXT.290 and/or ALK of the filtrate occurs, thereby reducing the frequency of replacing and regenerating ion-exchange resin without adversely affect the quality of the final caprolactam product, and reduce the amount of acid, base, and water generated.

SUMMARY OF THE INVENTION

One object of this invention is to provide a system for purifying an aqueous solution of crude caprolactam, which can reduce the frequency of replacing and regenerating ion-exchange resin.

Another object of the present invention is to provide a system for purifying an aqueous solution of crude caprolactam, the final caprolactam product obtained from which always meet the standards for caprolactam of industrial grade.

Another object of the present invention is to provide a system for purifying an aqueous solution of crude caprolactam, which can save the materials used for regenerating resin.

Another object of the present invention is to provide a system for purifying an aqueous solution of crude caprolactam, which can reduce the waste generated from regeneration of resin.

To achieve the above and other objects, the present invention provides a system for purifying an aqueous solution of crude caprolactam, comprising a filtration zone (A), which contains a filtration apparatus through which the aqueous solution of crude caprolactam is filtered to remove ionic impurities therein, so as to obtain caprolactam-containing filtrate (hereinafter also abbreviated as "filtrate");

an inspection unit (B) for judging whether the filtrate from the filtration zone (A) meets the preset inspection standards;

a purification zone (C) for receiving the filtrate meeting the preset inspection standards, and concentrating and purifying the filtrate to thereby form a final caprolactam product; and a first temporary storage tank (D) for receiving the filtrate not meeting the preset inspection standards, which is then mixed with the unfiltered aqueous solution of crude caprolactam and is delivered back to the filtration zone (A) after the mixing.

With the system according to the present invention, the frequency of replacing and regenerating the ion-exchange resin could be reduced without producing a caprolactam final product not meeting the preset inspection standard. Therefore, according to the present invention, the effective operating time of the ion-exchange resin apparatus can be extended to save starting material and to reduce waste.

This invention also provides a process for purifying an aqueous solution of crude caprolactam by using the above-mentioned system of the present invention, including the following steps of:

(a) delivering the aqueous solution of crude caprolactam to the filtration zone (A) containing a filtration apparatus through which the aqueous solution of crude caprolactam is filtered to remove ionic impurities therein, to thereby obtain a caprolactam-containing filtrate;

(b) judging whether the filtrate meets the preset inspection standards;

(c1) delivering the filtrate meeting the preset inspection standards to the purification zone (C), where the filtrate meeting the preset inspection standards is concentrated and purified to thereby obtain a final caprolactam product; and (c2) delivering the filtrate not meeting the preset inspection standards to the first temporary storage tank (D), and mixing the filtrate not meeting the preset inspection standards from the first temporary storage tank (D) with the unfiltered aqueous solution of crude caprolactam, and delivering the resulting mixture back to the filtration zone (A).

DESCRIPTION OF THE PREFERRED EMBODIMENTS

The objects and advantages of the present invention are further described in details by the following embodiments.

FIG. 1A shows the flow chart of the first embodiment of the present invention. The system, according to the first embodiment of the present invention, includes a filtration zone 100, an inspection unit 130, a purification zone 200 and a first temporary storage tank 300. A filtration apparatus is located in the filtration zone, such as ion-exchange resin apparatus set 110, which removes ionic impurities from aqueous solution of crude caprolactam by adsorption using resin, to obtain caprolactam-containing filtrate. An aqueous solution of crude caprolactam, obtained by the Beckmann reaction, which contains 30% to 40% of caprolactam, water and impurities, is delivered via a pipeline 10 to the filtration zone 100, where the aqueous solution of crude caprolactam is filtered through a filtration apparatus, for example, an ion-exchange apparatuses set 110, to remove ionic impurities in the aqueous solution, thereby obtaining a caprolactam-containing filtrate. As shown in FIG. 1B, the ion-exchange apparatuses set 110 is composed of two ion-exchange apparatuses 110a and 110b, which are connected in parallel and can be used alternately. When the ion-exchange apparatus 110a functions to filter the aqueous solution of crude caprolactam, the ion-exchange apparatus 110b stands by. Once the ion-exchange apparatus 110a cannot effectively functions, the apparatus 110b begins to function, thereby assuring that the filtration operation is not interrupted. The ion-exchange resin in the ion-exchange apparatus 110a is then regenerated through saltification by using a diluted acid or base solution, such that the adsorbed ionic impurities and organic impurities are desorbed from the resin. The regenerated resin is impregnated with demineralized water for backup use.

As shown in FIG. 1C, the ion-exchange apparatus 110a includes a tower 112 comprising an anion-exchange resin 112 that is connected in parallel, a tower 114 comprising a cation-exchange resin and a tower 116 comprising an anion-exchange resin. The three components. The anion-exchange resin can remove sulfate ions from the aqueous solution of crude caprolactam, whereas the cation-exchange resin can remove ammonium ions, thereby achieving the object of removing ionic impurities in the aqueous solution of crude caprolactam. In addition, the organic impurities in the aqueous solution of crude caprolactam can also be partially removed by the adsorptive action of the ion-exchange apparatus. The adsorption by the ion-exchange resin is preferably performed at a temperature not higher than 60, and more preferably not higher than 50. The flow rate of the aqueous solution of crude caprolactam through the ion-exchange apparatus is preferably between 3 to 6 BV/hr (1 BV=1 m$^3$ of solution per m$^3$ of resin).

The filtrate leaving the ion-exchange apparatus 110 in the filtration zone 100 is delivered via a pipeline 11 to the inspection unit 130, where the EXT.290 and the ALK of the filtrate are determined, for judging whether the filtrate meets the preset inspection standards, namely, EXT.290 below 0.15 and ALK below 0.5.

The EXT.290 is determined according to ISO7059 for caprolactam for industrial use. The ALK is determined by titrating the filtrate with standard HCl (0.01N) and calculating ALK from the volume of standard HCl used according to the following equation:

$$ALK = \frac{(V)(N)(1000)(100)}{(A)(caprolactam\%)}$$

wherein,

V is the volume of standard HCl used (ml)

N is the normality (0.01N) of standard HCl

A is the weight (g) of the sample caprolactam % is percentage of caprolactam in the sample. In this embodiment, if the EXT. 290 and the ALK. of the caprolactam-containing filtrate is smaller than 0.15 and 0.5, respectively, the caprolactam-containing filtrate is delivered via a pipeline 12 to the purification zone 200, to concentrate and purify the aqueous solution of caprolactam by removing remaining water and impurities, to obtain a final caprolactam product. If the EXT. 290 and the ALK. of the caprolactam-containing filtrate is greater than 0.15 and 0.5, respectively, the caprolactam-containing filtrate is delivered via a pipeline 14 to a first temporary storage tank 300 for storage. When the EXT. 290 and the ALK. of the caprolactam-containing filtrate is lowered to fall into the acceptable range, the aqueous solution stored in the first temporary tank 300 is mixed with unfiltered aqueous solution of crude caprolactam, and is redelivered into the filtration zone 100 to remove ionic impurities from aqueous solution. The volumes of the aqueous solution in the first temporary storage tank 300 and the unfiltered aqueous solution of crude capralactam is preferably mixed in the ratio of 1:02 to 1:04, more preferably mixed in the ratio of 1:0.05 to 1:04. If the ratio is too low, the recovery period will be extended, which will possibly affect the next replacement. If the ratio is too high, the quality of purification will be adversely affected due to overloading.

In this embodiment, the EXT.290 and the ALK of the filtrate from the filtration zone 100 abruptly rise to a value near or above the preset upper limits (0.15 for EXT.290 and 0.5 for ALK), after about 2100 to 2500 metric tons of pure caprolactam (calculated from the weight and concentration of the aqueous solution of crude caprolactam) is obtained. As shown in FIG. 2, the EXT. 290 of the filtrate abruptly rises from below 0.1 to 0.15 or more, even up to 0.2 or more after about 2100 to 2500 metric tons of pure caprolactam is obtained, then soon decreases back to below 0.15; thereafter, the EXT.290 steadily and slowly rises and remains below 0.15 for a relatively long period of time. Similarly, the ALK of the filtrate abruptly rises from below 0.3 to near or above 0.5 after about 2100 to 2500 metric tons of pure caprolactam is obtained, then decreases back to below 0.5. Because the EXT. 290 and the ALK. of the caprolactam-containing filtrate are greater than 0.15 and 0.5, respectively, the caprolactam product obtained from the concentration and purification step no longer meet the inspection standards (i.e., the EXT. 290 being smaller than 0.05). Therefore, resin must be replaced before the EXT. 290 exceeds the limit, to avoid obtaining an aqueous solution not meeting the standard. However, if the frequency of replacement of the ion-exchange resin apparatus is too high, the production rate will be lowered, a large amount of materials will be consumed, and a large amount of waste will also be produced. This will increase the production cost. On the other hand, although the yield of caprolactam will increase if the frequency of replacement is lowered, the EXT. 290 and the ALK. of the aqueous solution will be greater than 0.15 and 0.5, respectively.

During the period that the EXT.290 and/or ALK of the filtrate abruptly rises, the final caprolactam product obtained from the purification zone as described below may not meet the standards for caprolactam of industrial grade. In order to avoid this, replacement of ion-exchange apparatus was performed before the EXT.290 and/or ALK of the filtrate exceeded their upper limits according to the conventional process. However, such frequent replacement of ion-exchange apparatus resulted in reduced productivity and regeneration of the replaced ion-exchange resin would consume large amount of acids or bases and produced large amount of waste, which, in turn, would result in increased production cost.

There is a period in which the EXT. 290 and the ALK. rise, and ultimately cause the final caprolactam product not meeting the standard during filtration of aqueous solution of caprolactam. But there will be a long period of time in which effective operation will take place to form caprolactam-containing filtrate meeting the standards. Thus, the system of the present invention stores the aqueous solution not meeting the standards in the first temporary storage tank, while continues to filter without a need to immediate pause the process to replace resin. Final caprolactam products will not fail to meet the standards due to the continuous filtering process. Therefore, the system of the present invention can extend the effective operation time of ion-exchange resin apparatus, and has the advantage of saving materials and reducing waste.

This invention also provides a process for purifying an aqueous solution of crude caprolactam by using the above-mentioned system, including the following steps:

(a) delivering the aqueous solution of crude caprolactam to the filtration zone 100 which contains an ion-exchange apparatus set 110 through which the aqueous solution of crude caprolactam is filtered to remove the ionic impurities therein, thereby obtaining caprolactam-containing filtrate;

(b) judging whether the filtrate meets the preset inspection standards;

(c1) delivering the filtrate meeting the preset inspection standards to the purification zone 200, where the filtrate meeting the preset inspection standards is concentrated and purified to obtain a final caprolactam product; and (c2) delivering the filtrate not meeting the preset inspection standards to the first temporary storage tank 300, and mixing the filtrate not meeting the preset inspection standards from the first temporary storage tank with the aqueous solution of crude caprolactam, and delivering the resulting mixture back to the filtration zone 100.

As stated above, the EXT. 290 and the ALK. can be used to judge if the caprolactam-containing filtrate has reached the preset purification standards. Furthermore, the filtrate meeting the preset inspection standards may be hydrogenated before the step (c1), thereby converting the unsaturated organic impurities therein to saturated organic compounds. The latter may be easier to be removed in the purification zone 200.

FIG. 3 shows a flow chart of the second embodiment of the present invention. As described in the first embodiment, an aqueous solution of crude caprolactam obtained from the Beckmann reaction, which contains 30% to 40% of caprolactam, water and impurities, is delivered via a pipeline 10 to the filtration zone 100, where the aqueous solution of crude caprolactam is filtered through an ion-exchange apparatus set 110. The filtrate leaving the filtration zone 100 is delivered to an inspection zone 130 to judge whether the filtrate meets the preset inspection standards. The filtrate meeting the preset inspection standards is delivered via the pipeline 12 to a hydrogenation apparatus 150, where the unsaturated organic impurities (those having double or triple bonds in the molecules) in the filtrate are converted to saturated organic compounds, which are easier to be removed in the subsequent purification step. The filtrate after hydrogenation is delivered via a pipeline 18 to the purification zone 200, where the filtrate after hydrogenation is concentrated and purified to remove water and the residual impurities therein, thereby obtaining a final caprolactam product. The filtrate not meeting the preset inspection standards is delivered via the pipeline 14 to the first temporary storage tank 300. When the EXT.290 and the ALK. of the filtrate from the filtration zone 100 decrease back to below their preset upper limits after abrupt rising, the filtrate not meeting the preset inspection standards in the first temporary storage tank 300 is mixed with the aqueous solution of crude caprolactam via a pipeline 16 and delivered back to the filtration zone 100.

FIG. 4 shows a flow chart of the third embodiment of the present invention. An aqueous solution of crude caprolactam is delivered via the pipeline 10 to the filtration zone 100, where the aqueous solution of crude caprolactam is filtered through the ion-exchange resin apparatus set 110 to remove ionic impurities therein. The filtrate leaving the filtration zone 100 is delivered to the inspection zone 130 to judge whether the filtrate meets the preset inspection standards. The filtrate meeting the preset inspection standards is delivered via the pipeline 12 to the hydrogenation apparatus 150, where the unsaturated organic impurities (i.e. those having double or triple bonds) contained in the filtrate are converted to the saturated organic compounds, which is easier to be removed in the subsequent purification step. The filtrate after hydrogenation is delivered via the pipeline 18 to the purification zone 200, where the filtrate after hydrogenation is concentrated and purified to remove water and residual impurities therein, thereby obtaining the final caprolactam product. The purification zone 200 includes a vaporization apparatus 210 for concentrating the filtrate, a buffer apparatus 220 for receiving the concentrated filtrate from the vaporization apparatus 210, and a distillation apparatus 230 for purifying the concentrated filtrate. In the vaporization apparatus 210, most of water in the filtrate is removed to form a concentrated filtrate containing a high concentration, for example, higher than 80%, preferably higher than 90%, and more preferably higher than 99%, of caprolactam. The concentrated filtrate formed in the vaporization apparatus 210 is delivered via a pipeline 20 to the buffer apparatus 220, then delivered via a pipeline 22 to the distillation apparatus 230, where the residual water and impurities are removed to form the final caprolactam product. In the third embodiment of the present invention, the productivity of both the hydrogenation apparatus 150 and the vaporization apparatus 210 in the purification zone 200 will temporarily reduce to 40 to 60% of the original level when the filtrate leaving the filtration zone does not meet the preset inspection standards, and is delivered via the pipeline 14 to the first temporary storage tank 300; and will return to the original level once the filtrate leaving the filtration zone meets the preset inspection standards.

The system of the third embodiment may further include a second temporary storage tank 400 for storing the concentrated filtrate from the vaporization apparatus 210 during the period that the productivities of the hydrogenation apparatus 150 and the vaporization apparatus 210 temporarily reduce. The concentrated filtrate formed in the vaporization apparatus 210 is delivered via a pipeline 26 to the second temporary storage tank 400 during the period that the productivities of the hydrogenation apparatus 150 and the vaporization apparatus 210 reduce, and is delivered to the buffer apparatus 220, where the concentrated filtrate from the second temporary storage tank 400 is mixed with the concentrated filtrate originally in the buffer apparatus 220 in a ratio (by volume) of 1:0.05 to 1:0.4, preferably 1:0.2 to 1:0.4. The resulting mixture is delivered via pumping to the distillation apparatus 230.

BRIEF DESCRIPTION OF FIGURES

FIGS. 1A to 1C are related to the system according to the first embodiment of the present invention.

Figure 1C:
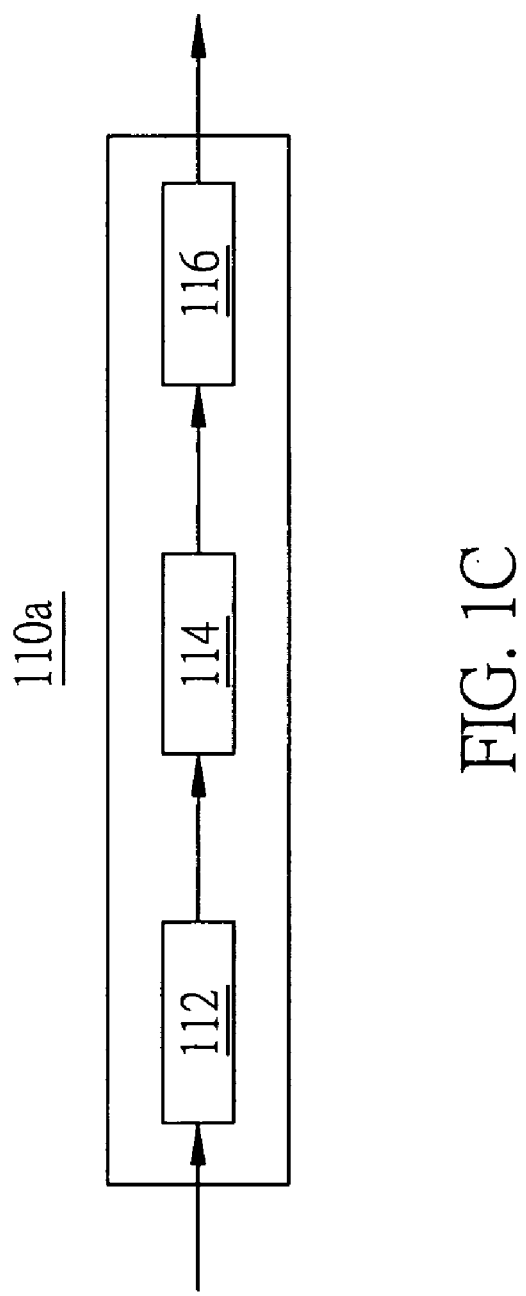
Figure 2:
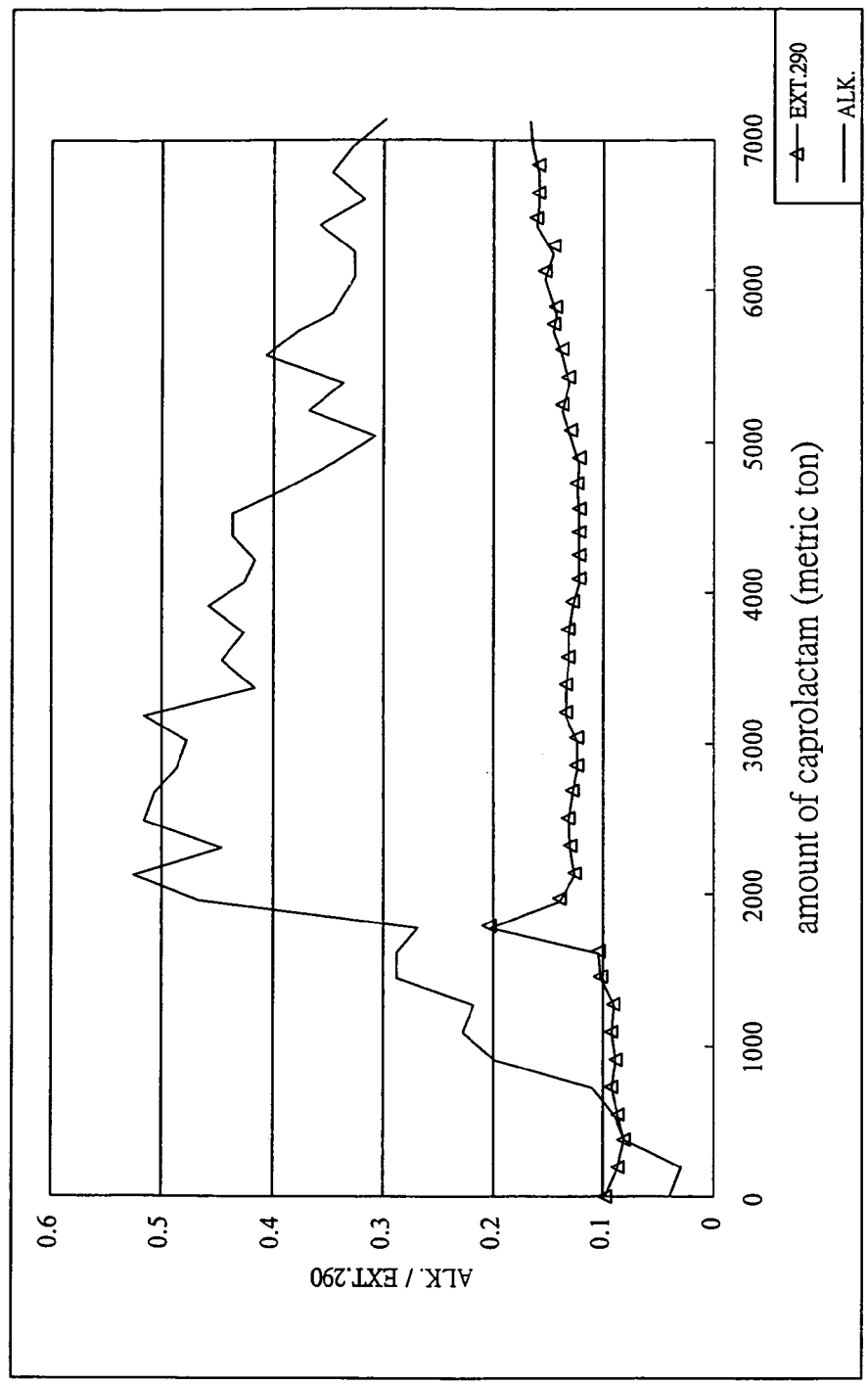
FIG. 2 is a graph showing the change of the EXT.290 and the ALK of the filtrate from the filtration zone when the ion-exchange apparatus functions in the first embodiment.
Figure 3:
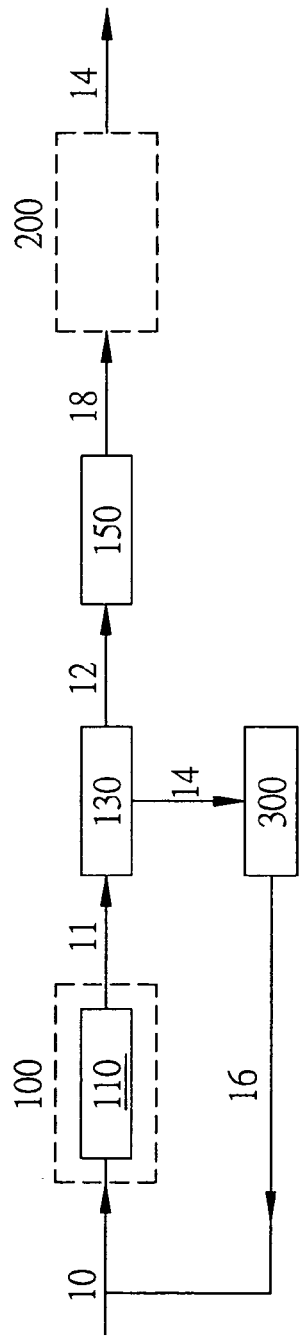
FIG. 3 shows the flow chart of the system according to the second embodiment of the present invention.
Figure 4:
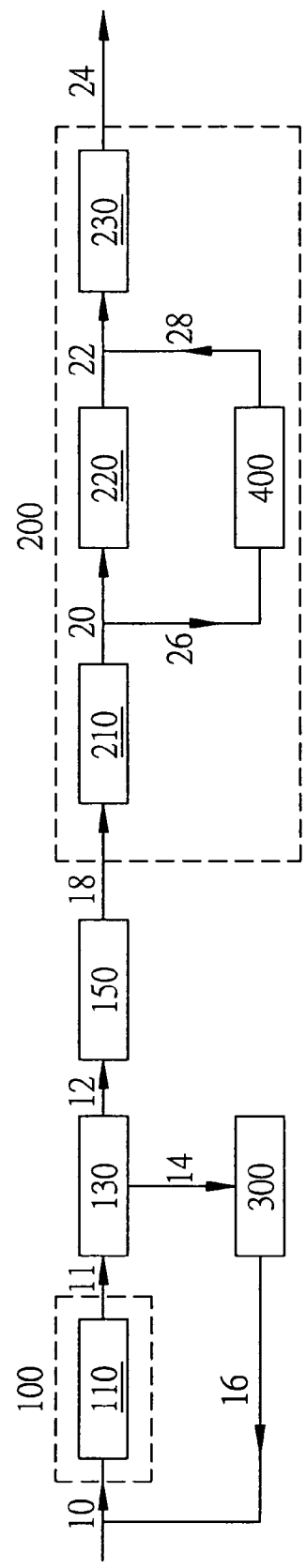
FIG. 4 shows the flow chart of the system according to the third embodiment of the present invention.
Figure 5:
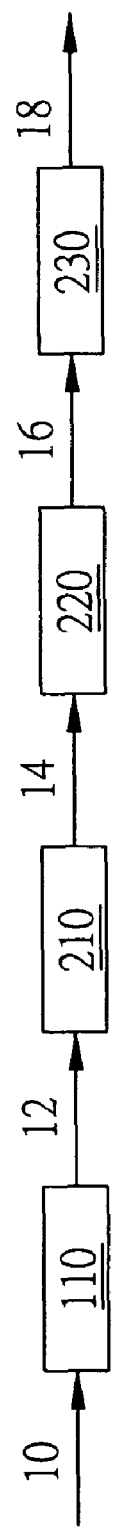
FIG. 5 shows the flow chart of the system of the conventional system.

What is claimed is:

1. A system for purifying an aqueous solution of crude caprolactam, comprising
   a filtration zone (A) having a filtration apparatus for filtering an aqueous solution of crude caprolactam to remove ionic impurities therein, so as to obtain caprolactam-containing filtrate, wherein the filtration apparatus is an ion-exchange apparatus set;
   an inspection unit (B) for judging whether the filtrate from the filtration zone (A) meets preset inspection standards;
   a purification zone (C) for receiving the filtrate meeting the preset inspection standards, and concentrating and purifying the filtrate to thereby form a final caprolactam product, wherein the purification zone (C) comprises:
      (C1) a vaporization apparatus for concentrating the filtrate not meeting the preset inspection standards:
      (C2) a buffer apparatus for receiving the concentrated filtrate containing a high concentration of caprolactam from the vaporization apparatus (C1); and
      (C3) a distillation apparatus for distillating the concentrated filtrate containing a high concentration of caprolactam to form the final caprolactam product; and
   a first temporary storage tank(D) for receiving the filtrate not meeting the preset inspection standards, which is then mixed with the aqueous solution of crude caprolactam and delivered back to the filtration zone (A).

2. The system according to claim 1, wherein the filtrate not meeting the preset inspection standards from the first temporary tank (D) is mixed with the aqueous solution of crude caprolactam in a ratio (by volume) of 1:0.05 to 1:0.4.

3. The system according to claim 1, wherein the ion-exchange apparatus set includes at least two ion-exchange apparatus comprising an ion-exchange resin, which are connected in parallel and can be used alternately.

4. The system according to claim 1, wherein the ion-exchange apparatus set comprises a tower comprising anion-exchange resin, a tower comprising a cation-exchange resin and a tower comprising an anion-exchange resin.

5. The system according to claim 1, wherein the aqueous solution of crude caprolactam contains 30 to 40% of caprolactam, water, and impurities.

6. The system according to claim 1, wherein the preset inspection standards for the filtrate from the filtration zone (A) include absorbance at a wavelength of 290 nm being (EXT.290) below 0.15.

7. The system according to claim 1, wherein the preset inspection standards for the filtrate from the filtration zone (A) include an alkaline value (ALK) being below 0.5.

8. The system according to claim 1, further comprising a hydrogenation apparatus for converting unsaturated organic impurities in the aqueous solution of crude caprolactam to saturated organic compounds.

9. The system according to claim 1, wherein the concentrated filtrate contains higher than 80% of caprolactam.

10. The system according to claim 9, wherein the concentrated filtrate contains higher than 90% of caprolactam.

11. The system according to claim 10, wherein the concentrated filtrate contains higher than 99% of caprolactam.

12. The system according to claim 1, wherein when the filtrate from the filtration zone (A) does not meet the preset inspection standards and is delivered to the first temporary storage tank (C), the productivity of the vaporization apparatus (C1) in the purification zone (C) is temporarily reduced.

13. The system according to claim 12, further comprising a second temporary storage tank.

14. The system according to claim 13, wherein the second temporary storage tank is used to store the concentrated filtrate containing g high concentration of caprolactam which is formed during a period in which the productivity of the vaporization apparatus (Cl) is reduced.

15. The system according to claim 14, wherein the concentrated filtrate containing a high concentration of caprolactam from the second temporary storage tank is mixed wit the concentrated filtrate containing a high concentration of caprolactam from the buffer apparatus (C2), and is delivered via pumping to the distillation apparatus (C3).

16. The system according to claim 15, wherein the concentrated filtrate containing a high concentration of caprolactam from the second temporary storage tank is mixed with the concentrated filtrate containing a high concentration of caprolactam from the buffer apparatus (C2) in a ratio (by volume) of 1:0.05 to 1:0.4.

17. A process for purifying the aqueous solution of crude caprolactam by using the system according to claim 1, comprising the following steps:
   (a) delivering the aqueous solution of crude caprolactam to the filtration zone (A) having a filtration apparatus trough which the aqueous solution of crude caprolactam is filtrated to remove ionic impurities therein, so as to obtain caprolactam-containing filtrate;
(b) judging whether the filtrate meets the preset inspection standards;
(c1) delivering the filtrate meeting preset inspection standards to the purification zone (C), where the filtrate meeting the preset inspection standards is concentrated and purified, to thereby obtain a final caprolactam product; and
(c2) delivering the filtrate not meeting the preset inspection standards to the first temporary storage tank (D), and
(d) mixing the filtrate not meeting the preset inspection standards from the first temporary storage tank (D) with the aqueous solution of crude caprolactam, followed by delivering the resulting mixture back to the filtration zone (A).

18. The process according to claim 17, wherein the preset inspection standards for the filtrate from the filtration zone (A) includes absorbance at a wavelength of 290 an being (EXT.290) below 0.15.

19. The process according to claim 17, wherein the preset inspection standards for the filtrate from the filtration zone (A) includes an alkaline value (ALK) being below 0.5.

20. The process according to claim 17, further comprising a hydrogenation step for converting unsaturated organic impurities in the aqueous solution of crude caprolactam to saturated organic compounds.

21. The process according to claim 20, wherein the hydrogenation step is performed before the step (c1).

* * * * *